United States Patent [19]

Folkman et al.

[11] Patent Number: 5,401,721

[45] Date of Patent: * Mar. 28, 1995

[54] ACID-RESISTANT FGF COMPOSITION FOR TREATING ULCERATING DISEASES OF THE GASTROINTESTINAL TRACT

[75] Inventors: Moses J. Folkman, Brookline, Mass.; Koichi Kato, Kawabe, Japan

[73] Assignees: Takeda Chemical Industries, Osaka, Japan; Children's Medical Center, Boston, Mass.

[*] Notice: The portion of the term of this patent subsequent to Dec. 29, 2009 has been disclaimed.

[21] Appl. No.: 862,776

[22] Filed: Apr. 3, 1992

Related U.S. Application Data

[63] Continuation of Ser. No. 382,263, Jul. 20, 1989, Pat. No. 5,175,147, which is a continuation-in-part of Ser. No. 234,966, Aug. 19, 1988, abandoned.

[51] Int. Cl.⁶ .................. A61K 37/00; A61K 47/00; A01N 25/00
[52] U.S. Cl. ..................... 514/12; 514/21; 514/925; 514/926; 514/927; 514/928; 514/970; 514/777; 514/778
[58] Field of Search ............ 514/12, 21, 925–928, 514/970, 977–978

[56] References Cited

U.S. PATENT DOCUMENTS 4,296,100  10/1981  Franco ................ 424/465
4,745,098  5/1988   Michaeli ................ 514/2

FOREIGN PATENT DOCUMENTS 8601879  3/1987  WIPO.

OTHER PUBLICATIONS

Illustrated Stedman's Medical Dictionary, 24th ed., Williams & Wilkins, Baltimore 1982, p. 280.
The Merck Index, 9th ed., Merck & Co., Inc. Rahway, N.J., 1976, APP-1 A3.

*Primary Examiner*—Robert J. Hill, Jr.
*Assistant Examiner*—A. M. Davenport
*Attorney, Agent, or Firm*—David G. Conlin; David S. Resnick

[57] ABSTRACT

This invention describes pharmaceutical compositions and methods of treating ulcerating diseases of the gastrointestinal tract in mammals with an acid-resistant fibroblast growth factor compositions. Also described is the use of acid-resistant fibroblast growth factor compositions in the treatment of various other fibroblast growth factor-responsive conditions.

5 Claims, 4 Drawing Sheets

```
                          BspMI
         10         ↓ 20         30         40         50         60
AAGCTTACCT GCCATGTTTA ATCTGCCTCC CGGGAATTAC AAGAAGCCCA AACTCCTCTA 70         80         90        100        110        120
CTGCAGCAAC GGGGGCCACT TCCTGAGGAT TCTTCCGGAT GGCACAGTGG ATGGACAAG 130        140        150        160        170        180
GGACAGGAGC GACCAGCACA TTCAGCTGCA ACTCAGTGCG GAAAGCGTGG GGGAGGTGTA 190        200        210        220        230        240
TATAAAGAGT ACCGAGACTG GCCAGTACTT GGCAATGGAC ACCGACGGGC TTTTATACGG 250        260        270        280        290        300
CTCACAGACA CCAAATGAGG AATGTTTGTT CCTGGAAAGG CTGGAGGAGA ACCATTACAA 310        320        330        340        350        360
CACCTATATA TCCAAGAAGC ATGCAGAGAA GAATTGGTTT GTTGGCCTCA AGAAGAATGG 370        380        390        400        410        420
GAGCTGCAAA CGCGGTCCTC GGACTCACTA TGGCAGAAA GCAATCTTGT TTCTCCCCCT 430        440        450        460        470        480
GCCAGTCTCT TCTGATTAAT AAGGATCCGA ATTC
                         ↑
                       BamHI
```

FIG. I

ACID-RESISTANT FGF COMPOSITION FOR TREATING ULCERATING DISEASES OF THE GASTROINTESTINAL TRACT

The present application is a continuation of application Ser. No. 07/382,263, filed Jul. 20, 1989, now U.S. Pat. No. 5,175,147, which is a continuation-in-part of Ser. No. 07/234,966, filed Aug. 19, 1988, now abandoned.

The present invention relates to acid-resistant fibroblast growth factor compositions, and to methods of treating ulcerating diseases of the gastrointestinal tract in mammals with acid-resistant fibroblast growth factor compositions. This invention also relates to the use of acid-resistant fibroblast growth factor compositions in the treatment of various other fibroblast growth factor-responsive conditions especially where acid and/or heat labile fibroblast growth factor has comparatively less therapeutic value.

BACKGROUND OF THE INVENTION

Ulcerating diseases of the gastrointestinal tract, commonly referred to as peptic ulcers, are diseases in which there is a defect in the epithelium of the gastrointestinal tract. This type of defect usually occurs through the combined action of hydrochloric acid and pepsin. By definition, peptic ulcers penetrate to at least the submucosa; more superficial lesions are referred to as erosions. Peptic ulcers may occur in many locations of the gastrointestinal tract including the stomach, duodenum or esophagus, in Meckel's diverticulum, at the sight of a surgically created anastomosis, and, rarely, in the upper jejunum.

Twenty years ago, treatment of peptic ulceration consisted of bedrest, a bland diet, antacids, and/or surgical removal of the affected area. More recently, $H_2$-receptor antagonists have been used in the treatment of peptic ulcers. The two most commonly used $H_2$-receptor antagonists are ranitidine and cimetidine, both of which act therapeutically by inhibiting gastric acid secretion. The effectiveness and unwanted effects of these two antagonists has been extensively studied, e.g., by Thomas et al., in *Clinics in Gastroenterology*, Volume 13, Number 2, at pages 501-529.

While treatment with these antagonists has been widespread and relatively successful, many peptic ulcers do not respond to $H_2$-receptor antagonist therapy. For example, while the reasons are not clearly understood, some 20 to 30% of duodenal ulcers do not heal after four to six weeks of therapy with either cimetidine or ranitidine. Moreover, recurrence or relapse of the ulcerating condition is not uncommon with $H_2$-receptor antagonists.

Fibroblast growth factor (FGF), has been shown to be a potent angiogenic factor which, inter alia, is responsible for neovascularization in wound healing. There are two types of FGF, acidic fibroblast growth factor (aFGF) and basic fibroblast growth factor (bFGF). aFGF and bFGF are, however, acid and/or heat labile. Thus, prior to the present invention, the use of FGF in acid and/or heat environments such as in the treatment of peptic ulcers has not been possible.

SUMMARY OF THE INVENTION

In accordance with the present invention, there is provided a novel method of treating mammals having a disease which is FGF-responsive, which comprises administering to the mammal an effective amount of an acid-resistant FGF composition or a pharmaceutically acceptable salt thereof. Specifically, the present invention provides a method of treating mammals having an ulcerating disease of the gastrointestinal tract which comprises administering an effective amount of an acid-resistant FGF composition to the mammal. More specifically, the present invention provides a method for treating peptic ulcers and other diseases, especially those which would otherwise be responsive to FGF treatment but for existence of an acid environment.

Preferably, the acid-resistant FGF composition of the present invention is administered in a pharmaceutically acceptable vehicle in conjunction or in combination with one or more of the following: (a) stabilizing agents; (b) antisecretory agents such as $H_2$-receptor antagonists; (c) cytoprotective agents; and (d) antacids.

Acid-resistant FGF compositions in accordance with the present invention, when administered to mammals with ulcerating diseases of the gastrointestinal tract, result in virtually complete healing of the ulcer. When compared with the above-described $H_2$-receptor antagonists, the best result for the antagonists was less than or equal to result achieved with approximately 10% of the optimal amount of the acid-resistant FGF composition.

BRIEF DESCRIPTION OF THE DRAWINGS

FIG. 1 shows the base sequence of the cDNA which codes for the human acidic FGF in Example 4.

DETAILED DESCRIPTION OF THE INVENTION

Figure 2:
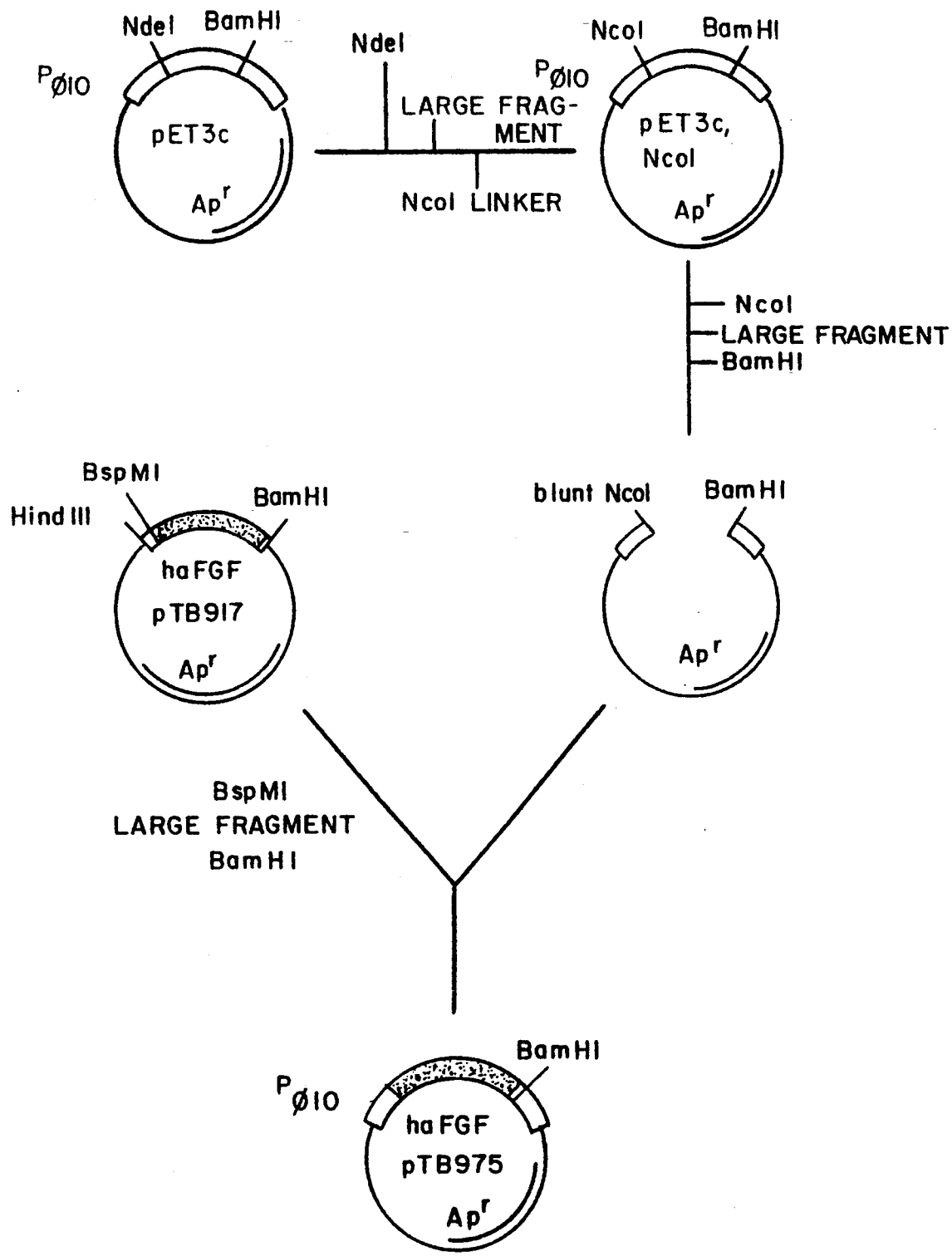
FIG. 2 shows the construction scheme of the plasmid TB975 in Example 4.

The present invention provides novel compositions and methods for the treatment and/or prevention of FGF-responsive diseases in mammals. The method, in its simplest form, comprises administering to the mammal an effective amount of an acid-resistant FGF composition or a pharmaceutically acceptable salt thereof. The invention also provides for certain pharmaceutical compositions comprising acid-resistant FGF or its salt, and one or more agents which stabilize, potentiate, or otherwise affect the therapeutic efficacy of acid-resistant FGF. Such agents include: (i) stabilizing agents such as glycosaminoglycan which include heparin, glucan sulfate such as dextran sulfate, sulfated cyclodextrins such as beta-cyclodextrin tetradecasulfate and $\beta$-1,3-glucan sulfate; (ii) antisecretory agents such as $H_2$-receptor antagonists (e.g., cimetidine, ranitidine, famotidine, roxatidine acetate), muscarine receptor antagonists (e.g., pirenzepine); (iii) cytoprotective agents such as spizofurone and prostaglandin derivatives, and; (iv) antacids such as aluminum hydroxide gel, sodium bicarbonate and sucralfate. Such agents may be administered either separately or as a component of the composition.

In accordance with the present invention, various ulcerating diseases of the gastrointestinal tract may be treated by administering to the mammal an effective amount of the acid-resistant FGF composition. Such ulcerating diseases include regional ileitis, ulcerated colitis and peptic ulcer (either duodenal or gastric).

The acid-resistant FGF composition of the present invention can also be used to treat other conditions in mammals which would be responsive to FGF therapy but for the existence of an acidic environment. For example, in cancer treatment of bladders, there often results ulcerations of that organ's tissue which could be treated with FGF if the FGF were acid-resistant. Bandaged wounds can also produce an acid environment which would respond to acid-resistant FGF. Other conditions in which there is an acid environment and which would otherwise be responsive to FGF therapy will be apparent to the skilled artisan.

The acid-resistant FGF composition of the present invention may be a composition of either aFGF or bFGF. aFGF and bFGF useful in practicing the present invention may be derived from a number of sources including mammals such as human, bovine, monkey, swine and equine.

Acid-resistant FGF compositions useful in practicing the present invention include: (i) acid-resistant native mammalian FGF such as aFGF (ii) native mammalian FGF which is stabilized by stabilizing agents; (iii) FGF which is modified to be acid-resistant; or (iv) modified FGF which is further stabilized by stabilizing agents.

The preferred acid-resistant FGF composition is one which includes a modified FGF such as a purified recombinant human basic FGF (rhbFGF) protein in which a mutation is induced ("mutein") by changing one or more of the four cysteines present at amino acid residues 25, 69, 87, and 92 of the mature protein to serine. In numbering the human bFGF-constituent amino acids, the N-terminal Pro is comprises the first amino acid. The most preferred acid-resistant FGF is the rhbFGF mutein CS23, the structure of which is more fully described in Senoo et al., Biochemical and Biophysical Research Communications, Vol. 151, No. 2, 701–708 (1988) and in U.S. Ser. No. 161,123, filed Feb. 18, 1988, which corresponds to EP-281,822 A2, the disclosures of which are hereby incorporated by reference herein. Other muteins which can be used in practicing the present invention and which are also described in these references include muteins in which amino acid(s) have been added, and where constituent amino acid(s) have been deleted or substituted.

While not to be bound by theory, it is believed that the substitution of neutral amino acids such as serine or alanine for cysteine residues in FGF stabilizes the FGF to heat, acid and certain enzymes which degrade FGF. This type of substitution is believed to cause minimal alteration to the structure and activity of the protein because the substitution of an oxygen atom (serine) for a sulfur atom (cysteine) prevents undersirable intermolecular disulfide bond formation at the mutation site.

Acid-resistant FGF in accordance with the present invention has been found to be highly stable in acid environments, particularly when used in conjunction with one or more of the stabilizing agents discussed in more detail below. Native mammalian FGF and FGF which is modified to be acid-resistant are very low in toxicity.

The preferred route of administration will depend on a number of factors including the condition being treated and patient convenience. For example, when used to treat ulcerating wounds of the bladder which are induced, for example, by radiation treatment or chemotherapy, then the acid-resistant FGF composition may be administered by urethral catheter. In treating ulcerating wounds of the gastrointestinal tract, the preferred route of administration is oral, e.g. by tablet, capsule, lozenge or chewable gum. Other routes of administration for diseases of the gastrointestinal tract include rectal, by enema and parenteral.

Preparation of acid-resistant FGF for administartion is accomplished by conventional techniques. For example, tablets and capsules are prepared by employing additives such as pharmaceutiaclly acceptable carriers (e.g. lactose, corn starch, light silicic anhydride, microcrystalline cellulose, sucrose), binders (e.g. alpha-form starch, methylcellulose, carboxymethylcellulose, hydroxypropylcellulose, hydroxy-propylmethylcellulose, polyvinylpyrrolidone), disintegrating agents (e.g. carboxymethylcellulose calcium, starch,low substituted hydroxypropylcellulose), surfactants (e.g. Tween 80 (Kao-Atlas), Pluronic F68 (Asahi Denka, Japan); polyoxyethylene-polyoxypropylene copolymer)), antioxidants (e.g. L-cysteine, sodium sulfite, sodium ascorbate), lubricants (e.g. magnesium stearate, talc), and the like.

Rectal preparations are also prepared by conventional techniques, for example, by employing an oleaginous base such as a higher fatty acid glyceride (e.g., cacao butter of the natural origin, Witepsols (a semisynthetic base, (Dynamite Nobel, Federal Republic of Germany)), a medium fatty acid glyceride (e.g. Miglyols (Dynamite Nobel)) or a vegetable oil (e.g., sesame oil, soybean oil, corn oil, cottonseed oil, olive oil).

When the composition is formulated into an injectable aqueous solution, the solution is prepared by conventional methods using a solvent such as an aqueous solvent (e.g., distilled water, physiological saline, Ringer's solution), or oily solvent (e.g., sesame oil, olive oil). If desired, one or more additives may be employed. Such additives include a dissolution aid (e.g. sodium salicylate, sodium acetate), buffer (e.g., sodium citrate, glycerine), isotonizing agent (e.g., glucose, invert sugar), stabilizers (e.g., human serum albumin, polyethylene glycol), preservatiave (e.g., benzyl alcohol, phenol) or analgesics (e.g., benzalkonium chloride, procaine hydrochloride).

When the composition is formulated into a solid preparation for injection, the preparation can be produced by routine methods using, for example, a diluent (e.g., distilled water, physiological saline, glucose), excipient (e.g., carboxymethylcellulose (CMC), sodium arginate), preservative (e.g., benzyl alcohol, benzalkonium chloride, phenol), or analegesics (e.g., glucose, calcium gluconate, procaine hydrochloride).

The dosage of acid-resistant FGF required is remarkably small when compared to other pharmaceutical agents such as the $H_2$-blockers, and depends on a number of factors including the condition being treated, whether or not it is used alone or in conjunction with stabilizing agents, antisecretory agents, cytoprotective agents and antacids, and the amount of food intake by the patient.

For example, when used to treat ulcerating diseases of the gastrointestinal tract in human adult patients, the amount of the acid-resistant FGF protein component of the composition to be administered orally is generally from about 0.1 $\mu$g to 30 mg per day, preferably from about 0.1 $\mu$g to 10 mg, more preferably from about 1.0 $\mu$g to 3 mg per day, and most preferably from about 10 $\mu$g to 300 $\mu$g per day. For oral administration, long to 150 $\mu$g of the rhbFGF mutein CS23 or its salt may be formulated as a tablet or a capsule together with a pharmaceutically acceptable carrier, diluent or other suitable vehicle. Such a formulation is beneficially administered one to four times daily to bring the dosage within the preferred range.

For certain diseases of the lower gastrointestinal tract such as peptic ulcers and ulcerated colitis, it is preferred that the acid-resistant FGF composition be coated with an enteric copolymer such as hydroxypropylmethylcellulose phthalate, cellulose acetate phthalate or a methacrylic acid copolymer to further protect the acid-resistant FGF from acid and digestive enzymes such as pepsin. This coated composition thus passes into the gastrointestinal tract such as the digestive tract and alimentary canal where its therapeutic value is optimized.

In accordance with another aspect of the present invention, it has been found that certain agents further stabilize and/or potentiate the activity of acid-resistant FGF. Such agents include antisecretory agents, cytoprotective agents, antacids, and stabilizing agents such as glycosaminoglycans and a group of compounds known as glucan sulfates. As the skilled artisan will appreciate, the relative amount of such stabilizing-/potentiating agents to FGF may vary depending on a number of factors, including the agent used, patient's condition and administration route. In general, the ratio of such stabilizers to FGF by weight is between about 0.1 to 100, preferably 0.2 to 20, more preferably from about 0.5 to 4.

The preferred antisecretory agents are ranitidine and cimetidine. The amount of antisecretory agent used will vary in accordance with the above-described factors. For example, when used to treat peptic ulcers, one preferred composition includes from about 10 to 300 $\mu$g, preferably about. 100 $\mu$g of the rhbFGF CS23 mutein and from about 20 to 600 mg, preferably about 200 mg of the antisecretory agent.

The preferred antacids include aluminum hydroxide gel, sodium bicarbonate and sucralfate. The antacid may be taken in conjunction with the acid-resistant FGF or may be incorporated as one component of the acid-resistant FGF composition itself. The amount of antacid will generally be 0.5 to 5 g per treatment.

The amount of cytoprotective agent used will depend on a number of factors including the agent used. For the prostaglandin derivative the amount is generally between 2.5 to 5 $\mu$g per adult human, and in the case of spizofurone about 80 mg per adult human.

Stabilizing agents-which may be used in accordance with the present invention include glycosaminoglycans such as heparin, fragments of heparin, glucan sulfates such as dextran sulfate, cyclodextrin sulfate and $\beta$-1,3-glucan sulfate. Said glucan sulfate preferably has a sulfur content of not less than about 3% (w/w), more preferably between about 12 to 20% (w/w), and most preferably between about 16 to 20% (w/w). The preferred stabilizing agents are the glucan sulfates, and in particular dextran sulfate.

Glycosaminoglycan, has been previously described, for example, in Molecular Biology of the Cell, Garland Publishing Inc., New York, London, 1983. It is desirable that the glycosaminoglycan used in the present invention have about 0.1 to 3.0 sulfate groups per disaccharide unit, and that its molecular weight be in the range of from 1,000 to 100,000, preferably from 2,000 to 50,000. Examples of such glycosaminoglycans include heparin, heparan sulfate and dermatan sulfate.

Heparin is described, for example, in the Merck Index, 8th ed. 1983. The molecular weight of heparin ranges from about 5,000 to about 40,000.

Cyclodextrins are natural cyclic compounds consisting of six (alpha), seven (beta) or eight (gamma) D-glucose units linked by alpha(1→4) linkage. They have a donut-shaped molecular structure which provides a cavity whereby clathrates may form with guest molecules of suitable size.

Cyclodextrin sulfate is an ester resulting from the sulfonation of these cyclodextrins. Sulfonation is achieved by known methods, One preferred method of sulfonation is described in U.S. Pat. No. 2,923,704 and Japanese Patent Application Laid-open No. 36422/1975.

The sulfur content of cyclodextrin sulfate normally exceeds about 3% (w/w), and is preferably between about 12 to 24% (w/w). Such cyclodextrin sulfates are also very soluble in water.

The degree of sulfonation of cyclodextrin sulfate for the present invention may be at any level exceeding 12% (w/w) as calculated as sulfur content. Cyclodextrin sulfate containing about 16 to 21% (w/w) sulfur is particularly advantageous.

The alpha, beta, and gamma cyclodextrin sulfate salts are all usable as stabilizing agents of FGF protein component in accordance with the present invention. $\beta$-cyclodextrin salts such as beta-cyclodextrin tetradecasulfate are preferred.

$\beta$-1,3-glucan sulfate used in the present invention is produced by sulfonating $\beta$-1,3-glucan. $\beta$-1,3-glucan is produced by microorganisms belonging to the genus Alcaligenus or Agrobacterium, has straight chains, is water-soluble and is thermogelable. Processes for purifying various glucans are described in Ebisu et al., Journal of Bacteriology pp. 1489-1501, 1975.

Curdlan (also known as thermogelable polysaccharide PS, commercially available from Wako Pure Chemical Industries, Ltd. Japan) is known to be a water-insoluble, thermogelable, unbranched straight chain glucan which has $\beta$-(1→3) linkage alone and which is produced by microbial strains belonging to the genus Alcaligenes or Agrobacterium (see e.g., Japanese Patent Publication Nos. 7,000/1968, 32,673/1973 and 32,674/1973 and British Patent No. 1,352,938). The curdlan producers Alcaligenes faecalis var. myxogenes NTK-u strain, Agrobacterium radiobacter strain and Agrobacterium radiobacter U-19 strain are listed respectively under ATCC-21680, ATCC-6466 and ATCC-21679 in the American Type Culture Collection Catalogue of Strains, I, 15th edition, 1982.

Hydrolysates which are low molecular weight derivatives of curdlan may also be used. The method of its production is described in detail in Japanese Patent Application Laid-open No.83798/1980, or in U.S. Pat. No. 4,454,315.

$\beta$-1,3-glucan may have an average degree of polymerization ($\overline{DP}$) below 1000. In particular, its partial hydrolysate with a $\overline{DP}$ ranging from 6 to about 300 is recommended, and its partial hydrolysate with a DP from 15 to about 200 is preferred.

The sulfate of straight chain $\beta$-1,3-glucan for the present invention is an ester resulting from the sulfonation of the hydroxyl groups of $\beta$-1,3-glucan or its lower polymers; an ester with an average degree of substitution ($\overline{DS}$) of 0.5 to 3 per monosaccharide unit is normally used, and an ester with a $\overline{DS}$ of 1 to 2 is preferably used.

Sulfonation of straight chain $\beta$-1,3-glucan or its low molecular weight polymer can be achieved by the method described in Journal of Biological Chemistry, 239, 2986 (1964). The sulfur content of $\beta$-1,3-glucan sulfate is normally over 5% (W/W), preferably about 10 to 21% (W/W), and it is very soluble in water.

Examples of the preferred glucan sulfate, dextran sulfate, employable in the present invention include sulfate of dextran, the dextran being produced from sucrose by the action of microorganisms such as Leuconostoc mesenteroides.

Dextran sulfate is a partial sulfate of dextran whose principal structure is an alpha (1→6) linkage of glucose, and the sulfur content is usually not less than about 12%, preferably about 16 to 20%. The average molecular weight is in the range of from about 1,000 to 40,000,000, preferably in the range of from about 3,000 to 1,000,000 and the dextran sulfate is very soluble in water.

The glucan sulfate employable in the present invention may also be in the form of a salt. As the salt, any pharmaceutically acceptable cation may be employed, e.g., sodium, potassium, ammonium, trimethyl ammonium, and the like.

When bringing glucan sulfate into contact with the FGF protein component in an aqueous medium, it may be conducted by first adding glucan sulfate in the free state then by adding an adequate amount of an alkali or an acid to adjust the pH desirably. By the addition of an alkali, the glucan sulfate may take the form of a salt in the aqueous medium, or a mixture of free glucan sulfate and glucan sulfate in the salt form may co-exist.

When the FGF protein component of the present invention is brought into contact with glucan sulfate in an aqueous medium, it is preferably conducted in the presence of di- or tri-basic carboxylic acid to give an even more stabilized FGF. Examples of di-basic carboxylic acid include tartaric acid, maleic acid, malic acid, fumaric acid, etc. Examples of tri-basic carboxylic acid include citric acid, iso-citric acid, etc.

The above-mentioned carboxylic acids may also be in the form of a salt. It may also be possible that native carboxylic acid be added to an aqueous medium, to which is added an adequate amount of an alkali or an acid to adjust the pH desirably. By the addition of an alkali, the glucan sulfate may take the form of a salt in the aqueous medium, or a mixture of free glucan sulfate and glucan sulfate in the salt form may co-exist.

When FGF protein component is brought into contact with glucan sulfate in an aqueous medium, the ratio of glucan sulfate to the FGF protein component ranges from about 0.1 to 100 by weight, preferably from 0.2 to 20 by weight most preferably from 0.5 to 4 by weight.

The concentration of glucan sulfate in an aqueous medium ranges preferably from about 0.0005 to 5 w/v%, more preferably from about 0.01 to 1 w/v%. The concentration of acid-resistant FGF in an aqueous medium ranges preferably from about 0.0005 to 5 w/v%, more preferably from about 0.01 to 1 w/v%. The amount of the carboxylic acid is preferably such as its concentration in an aqueous medium ranges from 1 mM to 1M, more preferably from about 10 mM to 500 mM.

For bringing the FGF protein component into contact with glucan sulfate and further with carboxylic acid in an aqueous medium, mere mixing of these materials in the aqueous medium accomplishes the purpose.

As the aqueous medium, use is preferably made of distilled water, physiological saline, glucose solution, buffers such as phosphate buffer and Tris-hydroxymethyl-aminomethane-HCl buffer.

An aqueous solution of FGF protein component, an aqueous solution of glucan sulfate and an aqueous solution of carboxylic acid may be mixed or a mixture of these materials in solid form may be dissolved in water. The mixing of these materials is conducted at temperatures ranging from 0° to 40° C. and preferably at pH ranging from about 3 to 10, more preferably from about 5 to 9. The time required for mixing is usually in the range of from about 1 to 30 minutes. The resulting composition may be lyophilized, during which procedure a complex may be formed and recovered.

For separating and recovering resulting stabilized FGF composition, a gel-filtration method using Sephadex gel, etc. or an ion-exchange chromatography using DEAE- or CM- Toyopearl may be used. Alternatively, the stabilized FGF composition can be used as it is, without separation or recovery.

By the processes described above, a highly stabilized composition of FGF is obtained, which composition can be safely used to treat mammals such as humans, rats, guinea pigs, dogs, mice, and the like.

The invention will be further illustrated with reference to the following examples which will aid in the understanding of the present invention, but which are not to be construed as a limitation thereof.

The recombinant human basic FGF (rhbFGF) used in the following Examples 5, 6 and 7 was produced in the manner described in Example 1, 3, 6 or 8 of EP-237,966 employing a transformant Escherichia coli K12 MM294/pTB669 (IFP 14532, FERM BP-1281).

rhbFGF mutein CS23 used in the following Examples 1, 2, 3, 5, 6 and 7 was produced by the manner described in the above-referenced Biochemical and Biophysical Research Communications vol. 151, pages 701–708 (1988), and Reference Examples 1 and 2 and Examples 1, 6,7 and 24 of U.S. patent application Ser. No.161,123 which corresponds to EP-281,822 A2 employing a transformant Escherichia coli MM294/pTB 762 (IFO 14613, FERM BP-1645).

Recombinant human acidic FGF (rhaFGF) used in the following Example 6 was produced by the manner of Example 4 mentioned below.

EXAMPLE 1

In the following experiments, the animal model described by S. Szabo, MD in the American Journal of Pathology, pages 273–276, 1978, was used to induce duodenal ulcers in normal rats. Specifically, cysteamine was given at a dose of 25 milligrams per 100 grams of body weight (BW) orally by intragastric lavage 3 times on the same day. Twenty-four hours later, approximately 10% of the rats died of a perforated ulcer. By day 3, a small abdominal incision was made in each rat to determine if a duodenal ulcer was present. Rats without any external evidence of duodenal ulcer, approximately 1-2% of the surviving rats, were eliminated from the study. Thus, all rats entering the study had ulcers, and were randomized in order to prevent bias.

All of the rats used in the study began with a body weight of approximately 160 grams. The following results were obtained from four groups of rats treated for 21 days and sacrificed. All measurements were taken at the time of sacrifice after 21 days of therapy.

Group I

No FGF Therapy

Four rats with ulcers received no FGF therapy. The incidence, depth and area of their ulcers were statistically similar to 50 other untreated rats in studies previously carried out.

| Mean Ulcer depth* | = | 1.625 (S.D. = 1.302; S.E.M. = 0.460) |
|---|---|---|
| Mean Area of Ulcers | = | 8.83 mm² (S.D. = 9.75 S.E.M. = 3.45) |
| Body Weight | | 189 g |
| | | 176 g |
| | | 177 g |
| | | 180 g |
| | x̄ = | 182 g |

*"Mean Ulcer Depth" as used herein means as follows: 1 = a few cells deep into the epithelium; 2 = below the mucosa and into the muscle cells; 3 = through the muscle layer; and 4 = penetrated (just prior to perforation.

Group II rhbFGF mutein CS23 10 nanograms

A second group of four rats received rhbFGF mutein CS23 at 10 nanograms per 100 grams of body weight orally, twice a day. This dose was adjusted for the weight of each animal, twice each week.

| Mean Ulcer depth | = | 1.00 (S.D. = 1.414; S.E.M. = 0.707) |
|---|---|---|
| Mean Area of Ulcers | = | 3.14 mm² |
| Body Weight | | 232 g |
| | | 212 g |
| | | 204 g |
| | | 216 g |
| | x̄ = | 216 g |

Group III rhbFGF mutein CS23 100 nanograms

A third group of four rats received rhbFGF mutein CS23 at 100 nanograms per 100 grams of body weight orally, twice a day. Again, this dose was adjusted for the weight of each animal, twice each week.

| Mean Ulcer depth | = | 0.25 (S.D. = 0.5; S.E.M. = 0.25) |
|---|---|---|
| Mean Area of Ulcers | = | 0.392 mm² (all ulcers completely healed, except for one tiny ulcer still healing in one rat) |
| Body Weight | | 198 g |
| | | 205 g |
| | | 254 g |
| | | 215 g |
| | x̄ = | 218 g |

Group IV rhbFGF mutein CS23 500 nanograms

A final group of five rats received rhbFGF mutein CS23 at 500 nanograms per 100 grams of body weight orally, twice a day. Once again, this dose was adjusted for the weight of each animal, twice each week.

| Mean Ulcer depth | = | 0.6 (S.D. = 1.342; S.E.M. = 0.6) |
|---|---|---|
| Mean Area of Ulcers | = | 1.88 mm² |
| Body Weight | | 207 g |
| | | 214 g |
| | | 295 g |
| | | 196 g |
| | | 216 g |
| | x̄ = | 208 g |

As can be seen from the above data, orally administered acid-resistant rhbFGF mutein CS23 results in rapid healing of cysteamine-induced ulcers. Even the best combination of H-2 blockers produce results less than or equal to that obtained in the 10 nanogram/rhbFGF mutein CS23 group.

EXAMPLE 2 rhbFGF mutein CS23 was added to a Dulbecco MEM medium containing 10% fetal calf serum to obtain a concentration of 10 μg/ml, to which was further added a salt of dextran sulfate (from Seikagagu Kogyo, Japan) so that the final concentration of the latter was 25 μg/ml. This medium was incubated at 37° C. for 24 hours. The salts of dextran sulfate were sodium salts whose average molecular weight was 5,000, 7,500 or 500,000, respectively. As a control group, the same medium, to which no dextran sulfate sodium was added, was employed. The remaining activities after 24 hours are shown in Table 1. In the remaining control, no substantial mutein CS23 activity remained, while in the test groups, the FGF activity remained stable.

TABLE 1

| Additive | Remaining FGF activity (%) |
|---|---|
| Dextran sulfate sodium (average molecular weight 5,000) | 93 |
| Dextran sulfate sodium (average molecular weight 7,500) | 100 |
| Dextran sulfate sodium (average molecular weight 500,000) | 100 |
| Control | 6 |

From the above data, it can be seen that dextran sulfate protects the rhbFGF mutein CS23 from temperatures to which it would be exposed in treating mammals. In other words, by bringing dextran sulfate into contact with FGF in an aqueous medium, stabilized FGF can be obtained. This stabilized FGF can be formulated into pharmaceutical preparations which are resistant to heat, acid and enzyme reactions found in the gastrointestinal tract.

EXAMPLE 3

An aqueous solution (pH 7.4) containing 0.5 mg of rhbFGF mutein CS23, 0.23 mg of dextran sulfate sodium having an average molecular weight 7500, and 15 mg of sodium citrate per ml was prepared.

EXAMPLE 4

Production of acidic FGF

Human acidic FGF was produced by the manner mentioned below referring to the methods described in Biotechnology 5, 960 (1987), Journal of Biological Chemistry 263, 16471 (1988), and ICSU Short Report volume 8, Advances in Gene Technology: Protein Engineering and Production, Proceedings of the 1988 Miami Bio/Technology Winter Symposium, IRL Press, page 110.

(i) Construction of expression plasmid

The cDNA (FIG. 1), which codes for human acidic FGF, was chemically synthesized and inserted into a plasmid pUC18 (Methods in Enzymology, 101, 20–78

(1983)) to give plasmid pTB917. The plasmid pTB917 was cleaved with BspMI and the ends were blunted by the reaction of E. coli DNA polymerase I large fragment. Then, the DNA was digested with BamHI to give 0.45 Kb DNA fragment. As a vector DNA, pET3c (Studier, F. W. et al. Journal of Molecular Biology, 189, 113-130 (1986)) which carries φ10 promoter of T7 phage was employed. PET3c was cleaved with NdeI, and blunted by employing E. coli DNA polymerase I large fragment. Thereafter, the NcoI linker 5'-CCATGG-3' was ligated to this DNA using T4 DNA ligase. The resulting plasmid was cleaved with NcoI, blunted with E. coli DNA polymerase I large fragment, and thereafter cleaved with BamHI to remove S10 sequence. To that site the 0.45Kb BspMI-BamHI blunt-ended fragment was inserted by ligation with T4 DNA ligase to give plasmid pTB 975 (FIG. 2).

(ii) Expression of haFGF cDNA in E. coli

Escherichia coli MM294 was lysogenized with lambda phage DE3 (Studier, supra), in which the RNA polymerase gene of T7 phage had been recombined. Thereafter, the plasmid pLysS was introduced into E. coli MM294 (DE 3) to give E. coli MM294 (DE3)/pLysS. To this strain, plasmid pTB975 was introduced, whereby E. coli MM294 (DE3)/pLysS, pTB975 was obtained. The above transformant was cultivated in L-broth containing 35 µg/ml of ampicillin and 10 µg/ml of chloramphenicol at 37° C. When the Klett value was about 170, isopropyl β-D-thiogalactoside (IPTG) was added to the medium to 0.5 mM as the final concentration, and the cultivation was continued for a further 3 hours. The cells were harvested by centrifugation, washed with PBS, harvested again, and stored at −20° C.

(iii) Purification of haFGF

Figure 3:
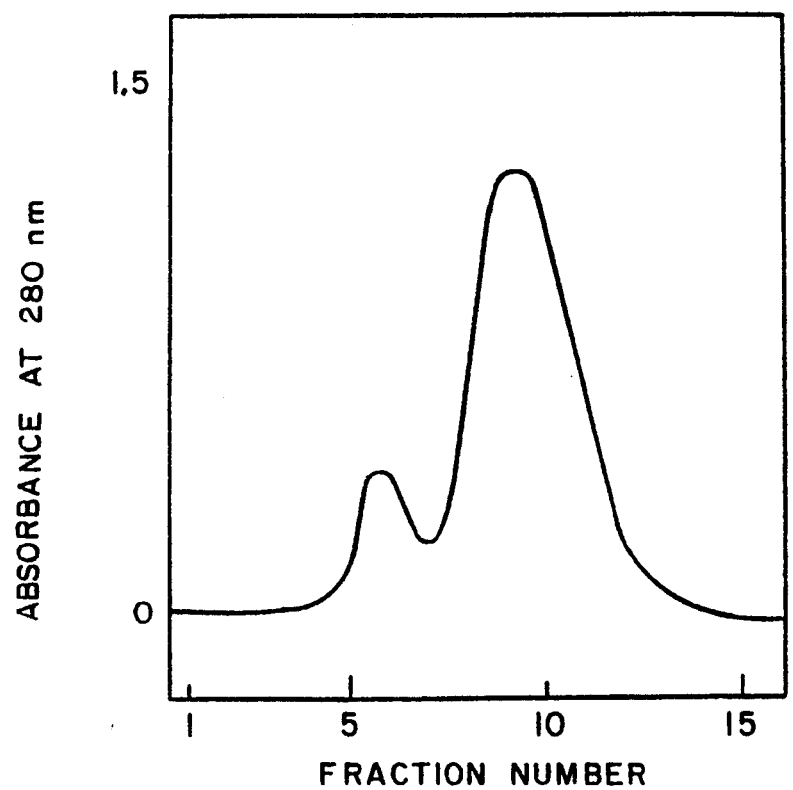
FIG. 3 to 5 show the elution patterns of the human acidic FGF in Example 4.
Figure 4:
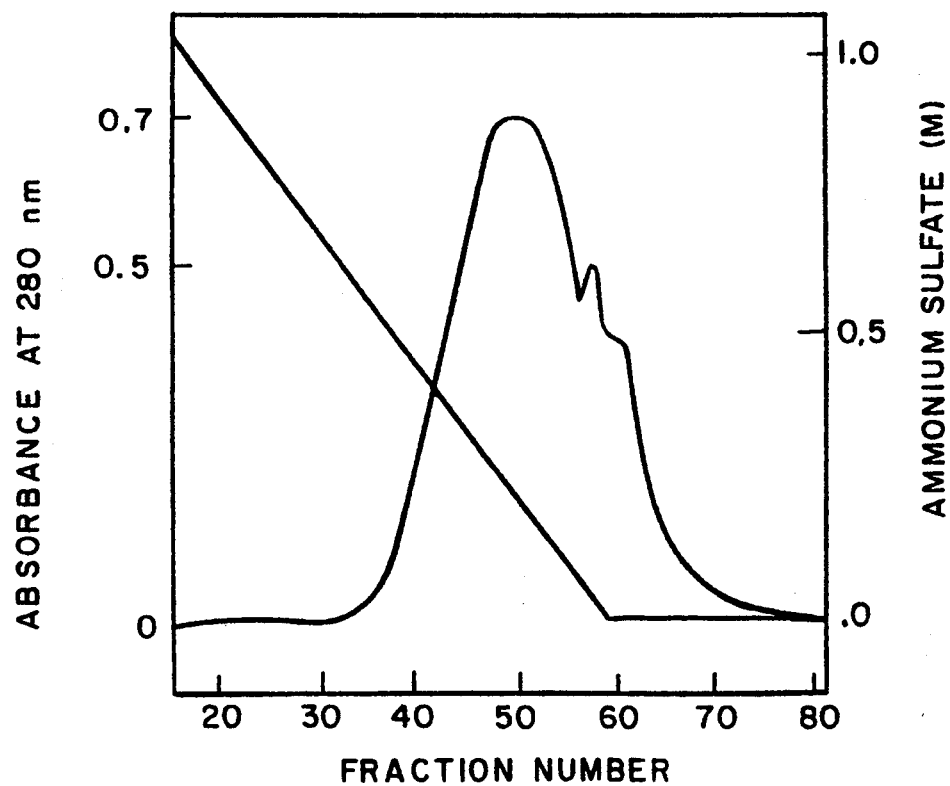

The cells collected from 1 liter of cultured broth were suspended in 100 ml of buffer containing 10 mM Tris-HCl (pH7.4), 10 mMEDTA, 0.6 M NaCl, 10% sucrose and 0.25 mM PMSF and then to the suspension egg white lysozyme was added at a concentration of 0.5 mg/ml. After keeping in an ice-bath for one hour, the mixture was incubated at 37° C. for 5 minutes, subjected to ultrasonication (20 seconds, twice), and subjected to centrifugation (SORVALL, 18000 rpm, 30 min., to 4° C.) to give a supernatant. This supernatant was mixed with buffer containing 20 mM Tris-HCl (pH7.4) and 1 mM EDTA under ice-cooling. The resulting mixture was passed through a heparin Sepharose column (diameter 2.5×4 cm) equilibrated with a buffer containing 20 mM Tris-HCl (pH 7.4), 1 mM EDTA, and 0.2M NaCl. After washing the column with 150 ml buffer containing 20 mM Tris-HCl (pH 7.4), 1 mM EDTA and 0.5M NaCl, protein was eluted with buffer containing 20 mM Tris-HCl (pH 7.4), 1 mM EDTA and 1.5 M NaCl. The eluates were fractionated to be 6 ml each, and the fractions (Nos. 8–11, total 24 ml) shown as the second peak were collected by monitoring with OD 280 (FIG. 3). To these fractions an equal amount of buffer (22 ml) containing 20 mM Tris-HCl (pH 7.4), 1 mM EDTA and 2M $(NH_4)_2SO_4$ was added. The mixture was passed through a phenyl Sepharose column (diameter 2.5×8 cm) equilibrated with buffer containing 20 mM Tris-HCl (pH 7.4), 1 mM EDTA and 1M $(NH_4)_2SO_4$ at a flow rate 0.5 ml/min. After washing the column with the buffer of the same components employed for equilibration, elution was performed on a linear gradient of 1M to 0M ammonium sulfate (flow rate 0.5 m./min., gradient time 200 min.) The fractions Nos. 40-55 (FIG. 4) were collected to give pruified human acidic FGF.

Figure 5:
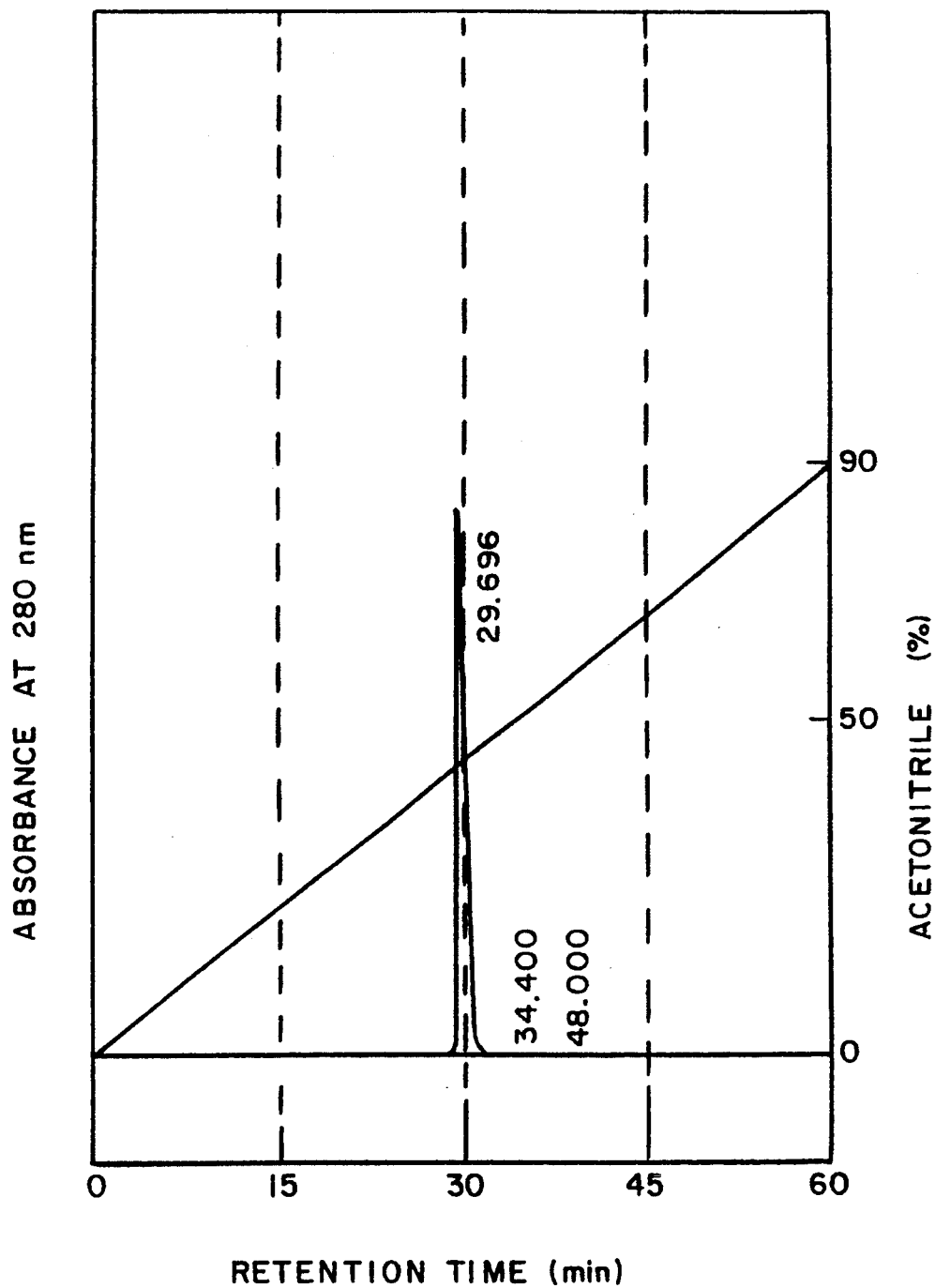

(iv) Reversed Phase C4 HPLC 0.25 ml of 1.2 mg/ml solution containing the purified haFGF obtained in step (iii) was mixed with 0.1% trifluoroacetic acid (TFA), and the mixture was applied to reversed phase C4 column (VYDAC, USA). Elution was performed on a linear gradient of 0% to 90% acetonitrile under the presence of 0.1% TFA to investigate the elution pattern. Flow rate 1 ml/min. Gradient time 60 min. The results are shown in FIG. 5.

(v) Biological Activity

Biological activity of the purified haFGF obtained in step (iv) was measured by the method of Sasada et al. Mol. Cell Biol. 8, 588–594 (1988), namely the activity was measured by the incorporation of [3H] thymidine in DNA in BALB/c3T3 cell. When sample was added, a solution of heparin (SIGMA, Grade I) was admixed to the culture medium and the sample, when necessary.

EXAMPLE 5

In the following experiments, the animal model described by K. Takagi et al. Jpn. J. Pharmacol., 19 p.418–426, 1969, was used to induce gastric, duodenal, or colonic ulcers in normal rats. Seven-week old male JcI:Sprague-Dawley rats weighing about 250 g were used. Rats were anesthetized with ether and an incision was made in the abdomen. A round metal mold, 6 mm in diameter, was placed in close contact with the serosal surface at the junction of the anterior wall of the corpus and antrum in the stomach, the duodenal wall, about 7 mm distal to pylorous, or the colonic wall, about 5 cm distal to the ileo-cecal junction. Glacial acetic acid (50 µl) was poured into the mold and was left in place for 20 seconds. After the acetic acid was removed, the treated surface was rinsed with 100 µl of saline and the abdomen was closed. The FGF compositions, suspended in 5% Gum arabic solution, were given orally twice a day (9 a.m. and 4 p.m.) for 6 consecutive days beginning the next day of the operation. The animals were sacrificed by $CO_2$ asphyxiation 7 days after the operation. The ulcerated areas ($mm^2$) and depth (grade 0 to about 3; 0: no lesion, 1: mucosal erosion, 2: moderate ulcer, 3: deep ulcer or perforation) were measured under a dissecting microscope with a 1 mm square grid eyepiece (×10). The ulcer index was obtained from the product of area and depth.

Acetic acid applied to the serosal surface of the stomach, duodenum and colon produced a round ulcer. As can be seen from Tables 2–4, the ulcer indices of control group in each ulcer at 7 days after operation were 6.7±1.1, 5.7±1.1 and 14.2±1.6, respectively. The control group received the vehicle alone comprising 50 mM citrate buffer (pH 7.0) containing 150 mM NaCl; the rhbFGF group received rhbFGF orally at 30 µg per kg of body weight; the CS23 group received CS23 (rhbFGF mutein CS23) orally at 30 µg per kg of body weight; and the CS23-DS group received a mixture of CS23 and DS (dextran sulfate) with an average molecular weight of 7500 at 30 µg and 13.8 µg, respectively, per kg of body weight. CS23 and CS23-DS accelerated the healing of the gastric, duodenal, and colonic ulcers; the effects on the duodenal and colonic ulcer being statistically significant (Tables 2–4). The effect of rhbFGF on the healing of the ulcers was less significant less than CS23 and CS23-DS.

TABLE 2

Effects of rhbFGF, CS23 and CS23-DS on the healing process of acetic acid-induced gastric ulcers in rats.

| Treatment | Dose (μg/kg, p.o) | No. of rats | Ulcer index | % Improvement in ulcer index |
|---|---|---|---|---|
| Control | | 8 | 6.7 ± 1.1 | — |
| rhbFGF | 30 | 8 | 5.8 ± 0.9 | 13 |
| CS23 | 30 | 8 | 4.3 ± 0.9 | 36 |
| CS23-DS | 30 | 8 | 3.6 ± 0.9 | 46 |

Results are expressed as mean ± s.e.

TABLE 3

Effects of rhbFGF, CS23 and CS23-DS on the healing process of acetic acid-induced duodenal ulcers in rats

| Treatment | Dose (μg/kg, p.o) | No. of rats | Ulcer index | % Improvement in ulcer index |
|---|---|---|---|---|
| Control | | 8 | 5.7 ± 1.1 | — |
| rhbFGF | 30 | 8 | 5.9 ± 1.4 | −4 |
| CS23 | 30 | 8 | 2.5 ± 0.5* | 56 |
| CS23-DS | 30 | 7 | 1.7 ± 0.4** | 70 |

Results are expressed as mean ± s.e.
*: $p < 0.05$,
**: $p < 0.01$ vs. Control (Student's t test)

TABLE 4

Effects of rhbFGF, CS23 and CS23-DS on the healing process of acetic-induced colonic ulcers in rats

| Treatment | Dose (μg/kg, p.o.) | No. of rats | Ulcer index | % Improvement in ulcer index |
|---|---|---|---|---|
| Control | | 8 | 14.2 ± 1.6 | — |
| rhbFGF | 30 | 8 | 14.0 ± 1.5 | 1 |
| CS23 | 30 | 8 | 8.0 ± 1.9* | 44 |
| CS23-DS | 30 | 8 | 7.3 ± 2.1 | 49 |

Results are expressed as mean ± s.e.
*: $p < 0.05$ s. Control (Student's t test)

EXAMPLE 6

In the following experiments, colonic ulcers were induced by the topical application of N-ethylmaleimide (NEM) on the surface of colonic mucosa. Seven-week old male Jcl:Sprague-Dawley rats weighing about 250 g were used. Rats were administered 50 μl of 3% NEM dissolved in 1% methyl cellulose intracolonally 6 cm oral portion from the anus using a Nelaton's cathether. The FGF compositions dissolved in 50mM citrate buffer (pH 7.0) containing 150 mM NaCl or 20 mM Tris-HCl buffer (pH 7.0) in a volume of 0.2 ml/rat were given intracolonally 7 cm from the anus using a Nelaton's cathether twice a day (9 a.m. and 4 p.m.) for 10 consecutive days beginning the day after inducement of the ulcer by NEM treatment. The animals were sacrificed by $CO_2$ asphyxiation 11 days after NEM treatment. The ulcerated area ($mm^2$) and depth (grade 0-3: 0: no lesion, 1: mucosal erosion, 2: moderate ulcer, 3: deep ulcer or perforation) were measured under a dissecting microscope with a 1 mm square grid eyepiece (×10). The ulcer index was obtained from the product of area and depth.

In Exp. 1, the control group received the vehicle alone comprising 50 mM citrate buffer (pH 7.0) containing 150 mM NaCl; the rhbFGF group received rhbFGF at 2 μg per rat; the CS23 group received CS23 at 2 μg per rat; and the CS23-DS group received a mixture of CS23 and DS with an average molecular weight of 7500 at 2 μg per rat and 0.92 μg per rat, respectively. In Exp. 2, the control group received 20 mM Tris-HCl buffer (pH 7.0) alone, rhaFGF group received rhaFGF prepared by the manner of Example 4 at 2 μg per rat.

As can be seen from Table 5, NEM applied to the mucosal surface of the colon produced severe deep ulcers. The ulcer index of control group 11 days after the administration of NEM was 231.6±51.1 in Exp. 1 and 191.6±84.5 in Exp. 2, respectively. All of rhbFGF, CS23, CS23-DS and rhaFGF and rhaFGF accelerated the healing of the colonic ulcers.

TABLE 5

Effects of rhbFGF, CS23, CS23-DS and rhaFGF on the healing process of NEM-induced colonic ulcers in rats

| Treatment | Dose (μg/rat) | No. of rats | Ulcer index | % Improvement in ulcer index |
|---|---|---|---|---|
| Exp. 1 | | | | |
| Control | | 8 | 231.6 ± 51.1 | — |
| rhbFGF | 2 | 9 | 167.6 ± 37.3 | 28 |
| CS23 | 2 | 9 | 108.4 ± 26.3* | 53 |
| CS23-DS | 2 | 9 | 79.4 ± 14.9* | 66 |
| Exp. 2 | | | | |
| Control | | 10 | 191.6 ± 84.5 | — |
| rhaFGF | 2 | 9 | 99.4 ± 25.2 | 48 |

Results are expressed as mean ± s.e.
*: $p < 0.05$ vs. Control (Student's t test)

EXAMPLE 7

In the following example, the animal model described in Example 1 was used to induce duodenal ulcers in normal rats. Female rats received 3 doses of cysteamine-HCl 25 mg/100 g p.o. Three days later rats with penetrating duodenal ulcers (as determined by laparotomy) were randomized into control and treatment groups. Rats (6-8/group) received (1) vehicle alone; (2) rhbFGF (wild) (wild type recombinant human bFGF); or (3) CS23 (acid-resistant mutein rhbFGF mutein CS23) at 100 ng/100 g by gavage twice daily until autopsy on day 21, when ulcers were measured and histologic sections taken. The experiment was repeated 3 times and the results pooled in Table 6:

TABLE 6

| Therapy | Rats with Ulcers | Ulcer Crater |
|---|---|---|
| Control | 89% | 9.8 ± 4.6 $mm^2$ |
| rhbFGF (wild) | 80% | 2.1 ± 1.3 $mm^2$ |
| | | ($p = 0.073$) |
| (CS23) | 33% | 1.7 ± 1.1 $mm^2$ |
| | | ($p = 0.063$) |

As can be seen from Table 6, histology of FGF-treated rats revealed: prominent angiogenesis, mild mononuclear cell infiltration, and dense granulation tissue in the ulcer bed; healed ulcers which were completely epithelialized; hypertrophic normal gastric and duodenal mucosa. These fidings were not observed in the rats treated with vehicle alone.

EXAMPLE 8

In the following example, the animal model described in Examples 1 and 7 was used to induce duodenal ulcers in normal rats. Female rats received 3 doses of cysteamine-HCl 25 mg/100 g p.o. Three days later rats with penetrating duodenal ulcers (as determined by laparotomy) were randomized into control and treatment groups. Rats (3-4/group) received (1) vehicle alone; (2) CS23 (acid-resistant mutein rhbFGF mutein CS23) at 100 ng/100 g; and (3) cimetidine at 10 mg/100 g by gavage twice daily until autopsy on day 21, when ulcers were measured and histologic sections taken. The results are shown in Table 7:

TABLE 7

| Therapy | Rats with Ulcers | Ulcer Crater |
| --- | --- | --- |
| Control | 100% | 10.6 ± 9.0 mm$^2$ |
| Cimetidine | 50% | 6.7 ± 2.9 mm$^2$ |
| (CS23) | 75% | 2.8 ± 1.9 mm$^2$ |

As can be seen from Table 7, use of the acid resistant FGF composition of the present invention in the treatment of ulcers results in marked improvement as compared with standard cimetidine therapy.

Other modifications of the above-described embodiments of the invention will be apparent to those skilled in the art and are intended to be within the scope of the following claims.

What is claimed is:

1. A pharmaceutical composition for ulcerating diseases of the gastrointestinal tract which comprises FGF, an antisecretory agent and a pharmaceutically acceptable carrier, wherein the ratio of the antisecretory agent to FGF by weight is between 0.1 to 100.

2. A pharmaceutical composition for ulcerating diseases of the gastrointestinal tract which comprises acid-resistant FGF, an antisecretory agent and a pharmaceutically acceptable carrier, wherein the ratio of the antisecretory agent to acid-resistant FGF by weight is between 0.1 to 100.

3. A pharmaceutical composition for ulcerating diseases of the gastrointestinal tract which comprises FGF or acid-resistant FGF, an antisecretory agent and a pharmaceutically acceptable carrier, wherein the ratio of antisecretory agent to FGF by weight is between 0.1 to 100 and wherein the antisecretory agent is selected from the group of cimetidine or ranitidine.

4. A pharmaceutical composition for ulcerating diseases of the gastrointestinal tract, which comprises FGF, an antisecretory agent and a pharmaceutically acceptable carrier, wherein the amount of FGF is about 10–300 μg, and the amount of the antisecretory agent is about 20–600 mg.

5. A pharmaceutical composition for ulcerating diseases of the gastrointestinal tract comprising about 10–300 μg of FGF, about 0.5–5 g of sucralfate and a pharmaceutically acceptable carrier.

* * * * *